United States Patent
Oden

(10) Patent No.: US 6,269,685 B1
(45) Date of Patent: Aug. 7, 2001

(54) VISCOSITY MEASURING USING MICROCANTILEVERS

(75) Inventor: Patrick Ian Oden, Plano, TX (US)

(73) Assignee: UT Battelle, LLC, Oak Ridge, TN (US)

(*) Notice: Subject to any disclaimer, the term of this patent is extended or adjusted under 35 U.S.C. 154(b) by 0 days.

(21) Appl. No.: 09/404,105

(22) Filed: Sep. 23, 1999

(51) Int. Cl.$^7$ ............... G01N 27/00; G01N 11/12
(52) U.S. Cl. ............... 73/54.23; 73/23.2; 73/24.06; 73/54.17
(58) Field of Search ............... 73/105, 515, 23.2, 73/24.06, 73, 54.06, 54.23, 54.24, 54.25, 514.11, 54.14, 54.17

(56) References Cited

U.S. PATENT DOCUMENTS

| | | | |
|---|---|---|---|
| 3,411,343 | * 11/1968 | Baird, Jr. | 73/54.17 |
| 3,898,871 | * 8/1975 | Gerin | 73/54.17 |
| 4,437,337 | 3/1984 | Fenrick | 73/54 |
| 4,464,928 | 8/1984 | Dealy | 73/54 |
| 4,862,735 | * 9/1989 | Williams et al. | 73/54.24 |
| 5,130,257 | * 7/1992 | Baer et al. | 73/24.06 |
| 5,345,816 | * 9/1994 | Clabes et al. | 73/105 |
| 5,445,008 | 8/1995 | Wachter et al. | 73/24.06 |
| 5,807,758 | 9/1998 | Lee et al. | 436/526 |
| 5,892,143 | * 4/1999 | Namerikawa et al. | 73/54.24 |
| 5,955,659 | 9/1999 | Gupta et al. | 73/54.01 |
| 6,016,686 | * 1/2000 | Thundat | 73/23.2 |
| 6,021,665 | * 2/2000 | Hayashi et al. | 73/105 |

FOREIGN PATENT DOCUMENTS

| | | |
|---|---|---|
| 0 305 133 A2 | 8/1988 | (EP) . |
| 1 476 935 | 6/1977 | (GB) . |
| WO 97/26527 | 7/1997 | (WO) . |

OTHER PUBLICATIONS

International Search Report for International Application No. PCT/US00/26104 (Nov. 24, 2000).

Nanofluid Handling by Micro–Flow–Sensor Based on Drag Force Measurements; V. Glass et al., pp. 167–172 (Feb. 7, 1993).

Oden, P. I. et al. Applied Physics Letters 68 (26) Jun. 24, 1996, pp. 3814–3816.*

Oden, Thomas et al. Appliance Manufacturer v45n4 Apr. 1997, pp. 57–58.*

* cited by examiner

Primary Examiner—Hezron Williams
Assistant Examiner—Michael Cygan
(74) Attorney, Agent, or Firm—J. Herbert O'Toole; Hardaway/Mann IP Group

(57) ABSTRACT

A method for the measurement of the viscosity of a fluid uses a micromachined cantilever mounted on a moveable base. As the base is rastered while in contact with the fluid, the deflection of the cantilever is measured and the viscosity determined by comparison with standards.

7 Claims, 5 Drawing Sheets

VISCOSITY MEASURING USING MICROCANTILEVERS

CROSS-REFERENCE TO RELATED APPLICATIONS

This application is related to new U.S. patent application, not yet assigned a serial number, bearing attorney docket number LME-65 025016/00058, Lockheed Martin ID number 0516.

This invention was made with Government support under Contract No. DE-AC05-96OR22464 awarded by the U.S. Department of Energy to Lockheed Martin Energy Research Corp., and the Government has certain rights in this invention.

BACKGROUND OF THE INVENTION

1. Field of the Invention

This invention relates to methods for measuring the viscosity of a fluid and related physical properties deriveable therefrom using a micromachined cantilever which may be optimized in geometry to the fluid being measured.

2. Prior Art

The atomic force microscope (AFM) was first demonstrated by Binnig and co-workers at IBM in Switzerland. In the AFM, the tip of a flexible cantilever stylus is rastered over the surface of a sample and the movement of the tip of the cantilever is monitored as a measure of minute forces characteristic of surfaces at the atomic level. Demonstration of this principle led to rapid development of microcantilevers [(Albrecht et al., *J. Vac. Sci. Technol*, 8, 3386 (1990)] The concept of micromechanical and microelectromechanical detection devices has been developed for a number of analytical uses. Wachter et al., U.S. Pat. No. 5,445,008 describes the use of vibrated microcantilevers having a chemical coating as a detector for the presence of specific chemical entities. Thundat, et al. in Appliance Manufacturer, April 1997, 57 (1997) and *Microscale Thermophysical Engineering* 1, 185 (1997) describe developments of the microelectromechanical sensors (MEMS) for the measurement of chemicals and physical phenomena including the use of sensors to determine concentrations of glycerol in water based on viscosity.

U.S. Pat. No. 5,719,342 to Thundat et al., addresses additional methods for analysis using MEMS devices particularly directed to induced stress in the microcantilever.

U.S. Pat. No. 5,130,257 to Bear et al., discloses a viscosity sensor fabricated using a surface transverse wave device for use in the measurement of viscosity.

Oden et al., *Appl. Phys. Lett.*, 68, 3814 (1996) discloses method for the measurement of viscosity using microfabricated cantilevers in a confined medium. The frequency of vibration of an isolated vibrating cantilever is measured in different solutions.

U.S. Pat. No. 5,494,639 to Grzegorzewski discloses a disposable biosensor which uses a vibrating member beneath a cell to accurately measure blood coagulation time as a function of viscosity.

The foregoing methods are attempts to find an alternative to the instruments most currently used to measure viscosity of both liquids and gases. These are instruments which perform the analysis by a comparison with a "control fluid." For this reason, measurements are still routinely done using instruments such as the Redwood viscometer, the Couette or rotational concentric-cylinder viscometer (MacMichael or Stormer viscometer), the Rotating Sphere viscometer, the Sayboult Falling Body viscometer, the Vibrating String viscosity meter and the thickness-sheer mode resonators. All of these methods require comparatively large volumes and bulky equipment. The need remains for a small reliable and inexpensive instrument which can measure the viscosity or specific density of small amounts of a liquid or gas and which can be used in difficult-to-access locations.

BRIEF DESCRIPTION OF THE INVENTION

It is an object of this invention to accurately determine the viscosity of a fluid in a simple and reliable manner.

It is a further object of this invention to provide an apparatus and a method which may be optimized to determine the viscosity of fluids of a general type, e.g. gases, liquids and slurries.

These and other objects of this invention may be achieved by moving a microfabricated beam structure of an optimized shape through a fluid and determining the viscosity based upon the bending of the cantilever structure. The base of the cantilever structure may be rastered over a small distance at varying rates or frequencies to determine the approximate viscosity and optimal raster frequency to obtain optimal accuracy for the specific fluid of interest.

DETAILED DESCRIPTION OF THE INVENTION

Prior art measurements of viscosity using microcantilevers were based upon vibrating the cantilever with a sinusoidal signal at or close to the resonance frequency of the structure. As indicated in the figures presented in our *Appl. Phys. Lett.* paper, the data obtained from a resonating cantilever becomes less distinct as the viscosity increases. It has now been discovered that accuracy may be improved if the cantilever is moved through the fluid by its base and the deflection of the tip in the fluid is used as a measure of the viscosity.

Unlike prior art methods wherein the cantilever was vibrated at or near its resonance frequency, the method of this invention observes the static deflection of the cantilever as it is moved through the fluid at a constant velocity.

According to this invention, the viscometer consists of a base, a prime mover, a cantilever and a method for detection. The cantilever is mounted onto the base either integrally or detachably. The base is attached to a prime mover. The detection system may be mounted to the base or the prime mover, depending upon the detection method selected.

As a base, a material may be used which is the same as or different from the cantilever. In a first embodiment, the base may be made of the same ceramic or semiconductor material as the cantilever and micromachined with the cantilever to obtain the desired shape. Alternatively, the base may be made from an indifferent material and adhesively attached or welded to the cantilever.

The prime mover is a oscillatory device such as a piezoelectric transducer. The prime mover is attached to a fixed frame within or immediately adjacent the fluid to be measured through mechanical or adhesive means. Likewise, it is attached to the base mechanically or adhesively.

The cantilever is a micromachined ceramic such as that described in U.S. Pat. Nos. 5,445,008 and 5,719,324. In general, fabrication and micromachining methods used for the production of atomic force microscope probes and the construction of semiconductor devices in the electronics industry are suitable for the practice of this invention. Nonlimiting examples of materials suitable for the cantilevers of this invention include silicon, silicon carbide, silicon nitride, germanium, gallium arsenide, gallium phosphide, cadmium selenide, cadmium sulfide, zinc oxide, titanium dioxide, tin oxide, and aluminum oxide. Through various deposition and etching techniques, the shape of the cantilever may be adapted to be more responsive to the viscosity of the fluid being measured. For example, a cantilever having a large frontal area distal to the base and a narrower intermediate portion will be more responsive to fluids having a very low viscosity such as helium in a partial vacuum. Alternatively, a small tip and thicker shank, such as a triangular cantilever, may be more suitable for a very viscous material such as olive oil.

Figure 1A:
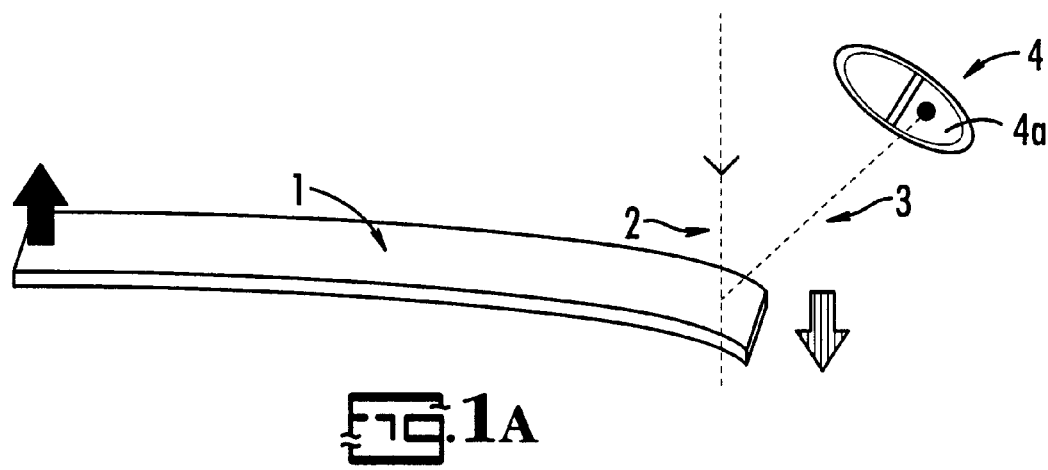
FIGS. 1(*a*) and 1)*b*) illustrate schematically the measurement of the deflection of a cantilever using a laser beam and split-segment photodetector.
Figure 1B:
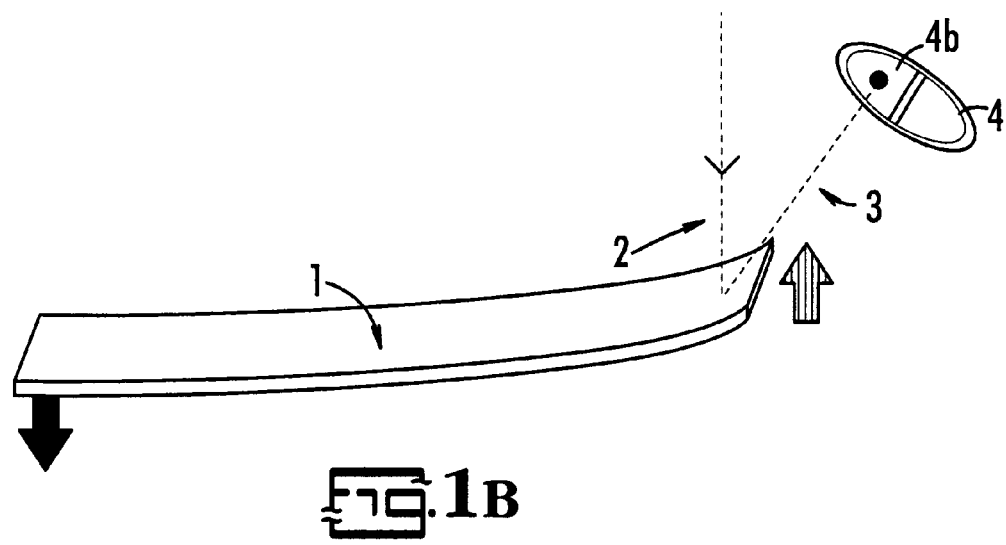

The method of detection may be by reflected light as illustrated in FIGS. 1(a) and 1(b) A laser beam 2 emitted from a laser diode is impinged upon the tip of the microcantilever 1 and the location of the tip determined by the reflected light 3 using a split-segment photodetector 4 (segments 4a and 4b), in the manner disclosed in U.S. Pat. Nos. 5,445,008 and 5,719,324.

Figure 2A:
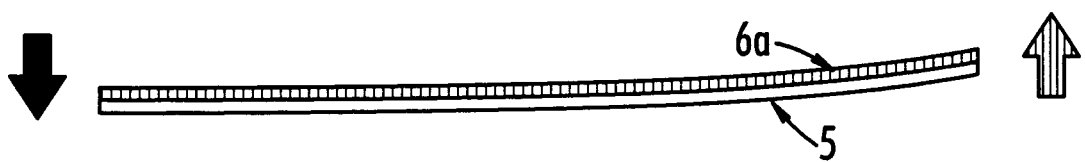
FIGS. 2(*a*) and 2(*b*) illustrate a method for measuring viscosity using a piezoresistive coating on the cantilever.
Figure 2B:
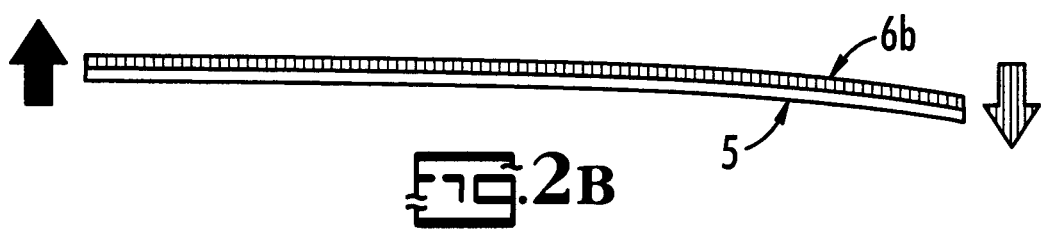

The position of the cantilever may be determined by a piezoresistive method as illustrated in FIGS. 2(a) and 2(b). The change in resistivity of the piezoresistive coating 6 on the cantilever 5 provides a measure of the degree and direction of the bending compressed 6(a) or stretched 6(b). Alternatively, the cantilever may be doped during fabrication to form a section which is piezoresistive.

Figure 3:
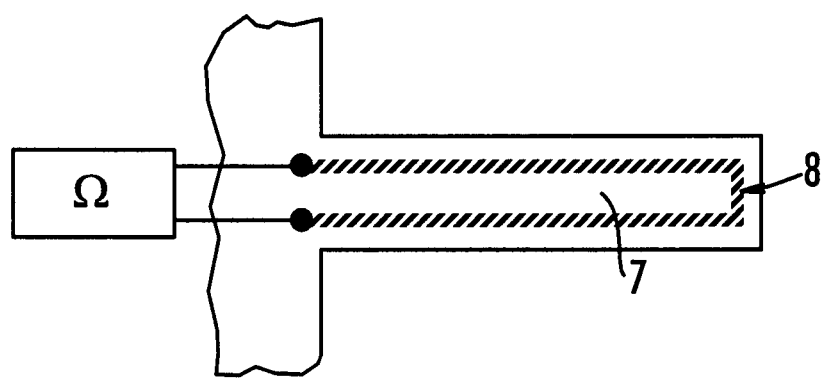
FIG. 3 illustrates an embodiment wherein the movement of the cantilever is detected using a piezoresistive track on the surface of the cantilever and monitoring the change in resistance resulting from bending.

Alternatively, a piezoresistive track 8 may be formed on the surface of the microcantilever 7 and the resistance measured as shown in FIG. 3.

Figure 4A:
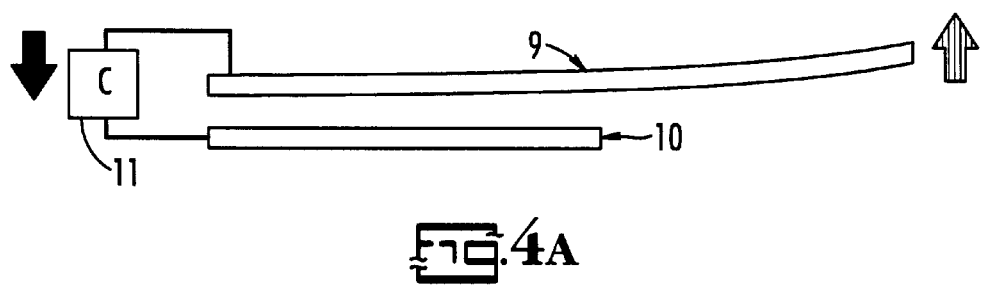
FIG. 4 illustrates a method for detection based upon the change in capacitance between a rigid reference plate and a flexed cantilever.
Figure 4B:
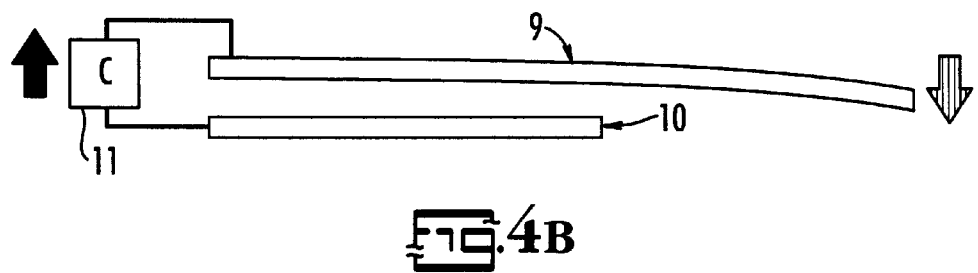

A capacitance method using a configuration such as that shown in FIG. 4(a) and 4(b) offers advantages because an unitary structure is rastered during the measurement. The capacitance is measured between the cantilever 9 and a reference plate 10 using conventional circuitry 11. The device according to this embodiment is easily calibrated.

Figure 5:
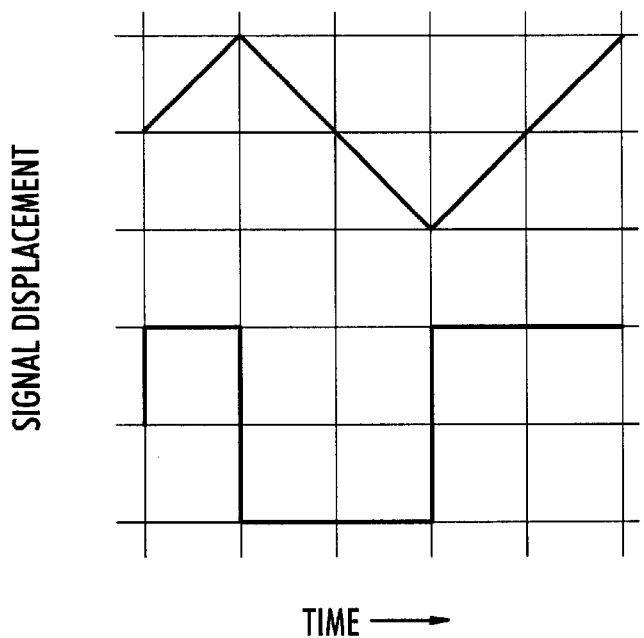
FIG. 5 illustrates the relationship between the displacement of the tip of the cantilever and the detection signal which is observed.

In the practice of measuring the viscosity, the cantilever base is mounted on a support structure and rastered over a range of frequencies generated by a frequency generating circuit and passed to the cantilever driver such as a piezoelectric transducer. As the cantilever is moved in one direction at a constant speed, the very low mass microcantilever is bent to a constant angle. When the cantilever is stopped, the bending goes to zero. Returning to the starting point at the same rate provides a second measurement which is the same as or readily related to the first measurement (assuming a similar coefficient of drag Cd in each direction). The relationship between cantilever displacement and observed signal is shown in FIG. 5. The degree of bending increases with the velocity of movement for a single fluid and with the change of (increase in) viscosity when different fluids are compared.

The response of the microcantilever is monitored as described above and the response plotted against the raster frequency. A linear-linear plot of the data produces a straight line in the appropriate range of frequencies. From the straight line, the slope is easily calculated and compared to known standards.

The viscometer according to this invention may be calibrated against any standard or alternative method of viscometry. The practical utility of the device lies not in the determination of absolute viscosities, which have little intrinsic value, but in application to industrial processes. The small size of the device allows measurements of relative viscosities and changes in viscosity at remote or even hazardous locations. The device may be located in a process stream or side stream of a chemical process to monitor a rate of change or to identify excursions from desired conditions. The small size allows for measurement of local conditions before a comparable change can be documented in the bulk. For example, temperature changes in a lubricant develop more slowly than viscosity changes at the point where the overheated lubricant merges with the bulk of the lubricant volume. The Brix of a saccharide solution may be monitored at the point of mixing and changes in the rate of dissolution can be observed almost instantaneously. Process conditions in stirred reactors or in inline reactors may be monitored and the results used as input to control systems. Gas mixtures may be monitored for correct mixture ratios or pressures. As noted earlier, the shape of the microcantilever may be tailored to provide optimal response in the viscosity range of especial interest.

The invention will be described in the following examples which are be way of illustration only and not limiting of the inventive concept. Modifications apparent to those skilled in the art are consumed within the scope of the invention.

EXAMPLE 1

Figure 6:
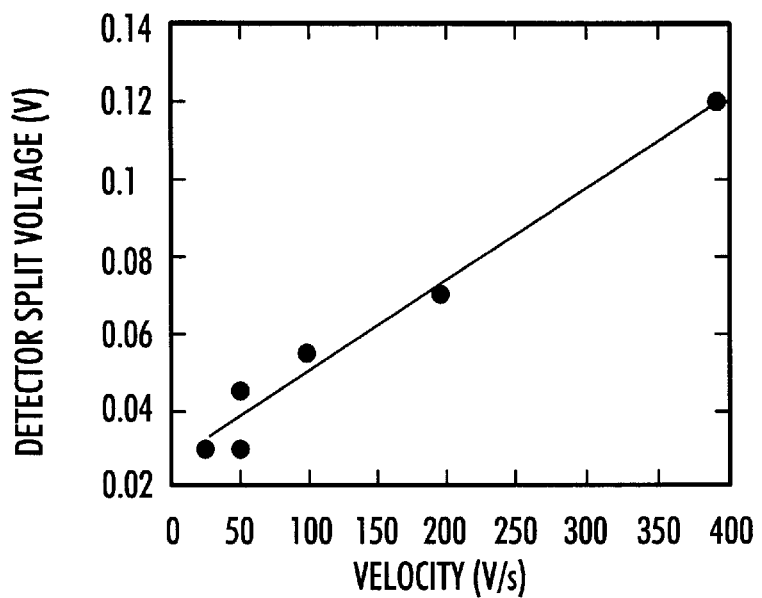
FIG. 6 is a plot of cantilever movement versus cantilever bending in mineral oil for low velocity movement.
Figure 7:
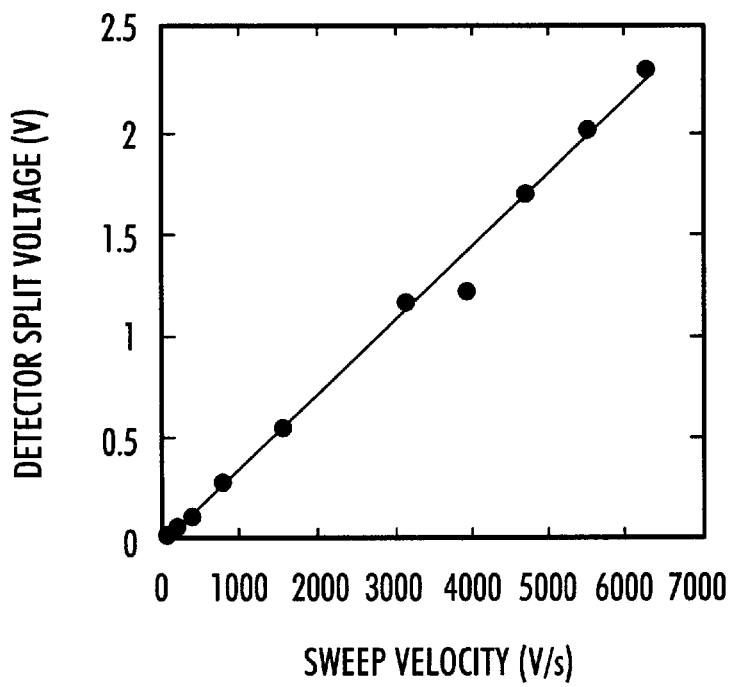
FIG. 7 is a plot of cantilever movement versus cantilever bending in minpral oil at medium velocity.
Figure 8:
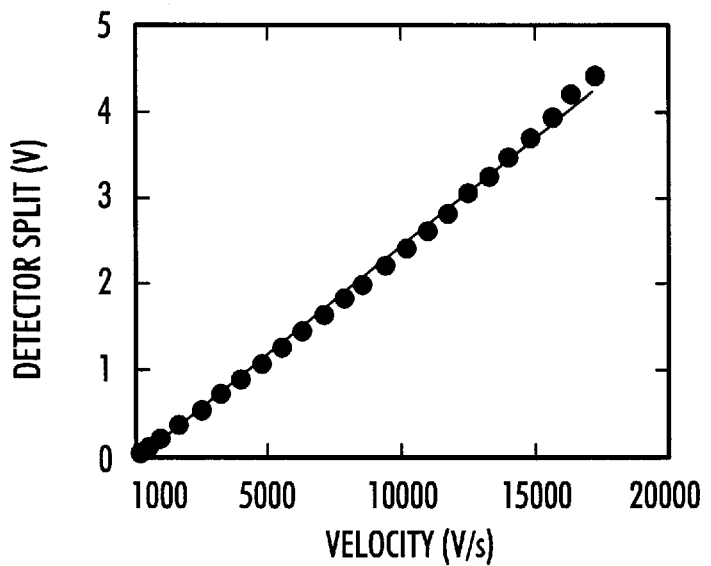
FIG. 8 is a plot of cantilever movement versus cantilever bending in mineral oil at high velocity.

A silicon nitride cantilever having a length of 220 micrometers, a width of 22 micrometers and a thickness of 0.6 micrometers was mounted on a base, attached to and driven by a piezoelectric transducer. A laser beam and split segment photodetector were placed so as to monitor the deflection signal off of the cantilever sensor. The device was placed in a well and the well filled with mineral oil to cover the entire sensor structure. The piezoelectric transducer is driven from 0 to 40 kHz by increasing the voltage and the deflection is measured a the detector split voltage. The data is displayed on a deflection monitoring system. The results are shown graphically in FIGS. 6, 7 and 8 for various rates of movement. The viscosities determined from the slopes of these curves is scalable to the actual viscosity of the solution in which the sensor is immersed.

EXAMPLE 2

Figure 9:
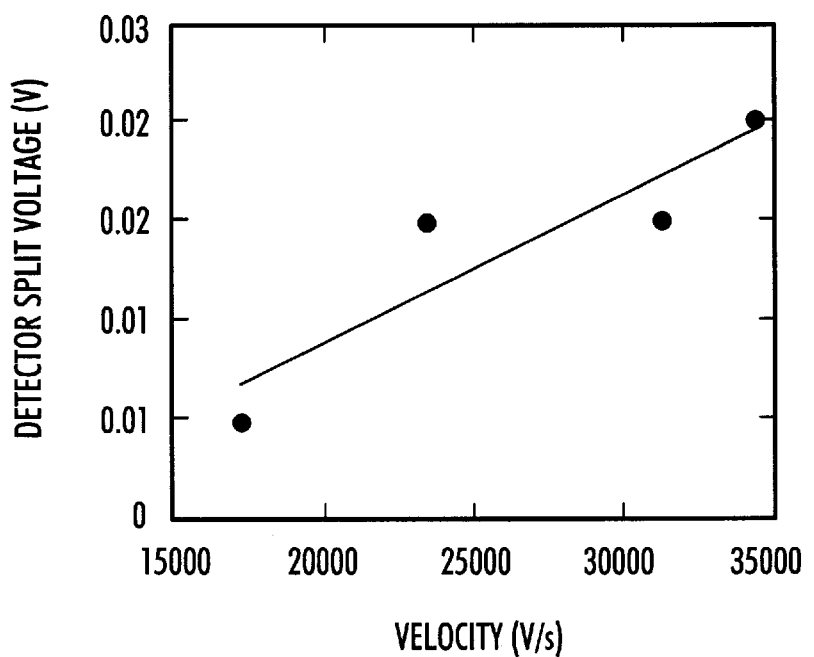
FIG. 9 plot of cantilever movement versus cantilever bending in air.

A silicon nitride cantilever having a length of 220 crometers, a width of 22 micrometers and a thickness of 0.6 crometers was mounted as described in Example 1 and used to asure the viscosity of air within an enclosure. The results are own in FIG. 9.

What is claimed is:

1. A method for the measurement of viscosity of a fluid comprising moving a microcantilever by its base in a fluid at a constant velocity, measuring the deflection ofthe tip ofthe cantilever, and comparing the deflection to the deflection under the same conditions in a fluid of known viscosity.

2. A method according to claim 1, wherein the microcantilever is formed by micromachining a substrate selected from the group consisting of silicon, silicon carbide, silicon nitride, germanium, gallium arsenide, gallium phosphide, cadmium selenide, cadmium sulfide, zinc oxide, titanium dioxide, aluminum oxide and tin oxide.

3. A method according to claim 1, wherein the fluid is selected from the group consisting of gasses, liquids and slurries.

4. A method according to claim 1 wherein the deflection is measured by optical means.

5. A method according to claim 1 wherein the deflection is measured by piezoelectric means.

6. A method according to claim 1 wherein the deflection is measured by piezoresistive means.

7. A method according to claim 1 wherein the deflection is measured by capacitive means.

* * * * *